United States Patent
Zhang (10) Patent No.: US 10,150,065 B2
(45) Date of Patent: Dec. 11, 2018

(54) EXTRACTION STRUCTURE, EXTRACTION MODULE, AND LIQUID PRETREATMENT DEVICE

(71) Applicant: Tianjin Anbang Jianhe Technology Co., Ltd., Tianjing (CN)

(72) Inventor: Qixiang Zhang, Weihai (CN)

(73) Assignee: TIANJIN ANBANG JINAHE TECHNOLOGY CO., LTD., Tianjing (CN)

( * ) Notice: Subject to any disclaimer, the term of this patent is extended or adjusted under 35 U.S.C. 154(b) by 120 days.

(21) Appl. No.: 15/298,872

(22) Filed: Oct. 20, 2016

(65) Prior Publication Data
US 2017/0326481 A1  Nov. 16, 2017

(30) Foreign Application Priority Data
May 16, 2016  (CN) .......................... 2016 1 0324081

(51) Int. Cl.
| | |
|---|---|
| B01D 33/42 | (2006.01) |
| B01D 33/74 | (2006.01) |
| B01D 33/01 | (2006.01) |
| B01D 17/00 | (2006.01) |
| G01N 1/34 | (2006.01) |
| G01N 1/40 | (2006.01) |

(52) U.S. Cl.
CPC ........... *B01D 33/42* (2013.01); *B01D 17/085* (2013.01); *B01D 33/015* (2013.01); *B01D 33/74* (2013.01); *G01N 1/34* (2013.01); *G01N 1/405* (2013.01); *G01N 2001/4016* (2013.01); *G01N 2001/4088* (2013.01)

(58) Field of Classification Search
CPC ....... B01D 33/42; B01D 33/74; B01D 33/015
USPC .... 210/323.2, 634, 635, 641, 643, 644, 283, 210/284, 290, 291, 314, 321.64, 490, 492, 210/502.1, 645, 648, 689
See application file for complete search history.

(56) References Cited

U.S. PATENT DOCUMENTS

| | | | |
|---|---|---|---|
| 4,890,485 A * | 1/1990 | Hsu ....................... | G01M 3/042 210/689 |
| 5,565,622 A | 10/1996 | Murphy | |
| 6,375,855 B1 | 4/2002 | Vassarotti | |

FOREIGN PATENT DOCUMENTS

| | | |
|---|---|---|
| CN | 2860578 Y | 1/2007 |
| CN | 101269274 A | 9/2008 |
| CN | 101279146 A | 10/2008 |

(Continued)

*Primary Examiner* — Madeline Gonzalez
(74) *Attorney, Agent, or Firm* — Fredrikson & Byron, P.A.

(57) ABSTRACT

Provided are an extraction structure, an extraction module, and a liquid pretreatment device relating to the liquid component testing technical field. The extraction structure comprises a cavity and a first pore passage. The extraction module comprises an extraction module body, successively bottom up, including a first cavity provided therein with a second filter layer, a first pore passage provided therein with a first filter layer, and a second cavity provided therein with an extractant layer and a porous filter disc; the first and second filter layers contain therein an expansive agent; and the diameter of the first filter layer is smaller than that of the second filter disc. The liquid pretreatment device comprises a storage tank, a transfer device and the extraction module. Between the transfer device and the extraction module is provided a filter membrane for filtering and supporting.

13 Claims, 5 Drawing Sheets

(56) References Cited

FOREIGN PATENT DOCUMENTS

| | | |
|---|---|---|
| CN | 101303278 A | 11/2008 |
| CN | 201168460 Y | 12/2008 |
| CN | 101995353 A | 3/2011 |
| CN | 201906484 U | 7/2011 |
| CN | 102872834 A | 1/2013 |
| CN | 202869877 U | 4/2013 |
| CN | 203385613 U | 1/2014 |
| CN | 203954733 U | 11/2014 |
| CN | 204952351 U | 1/2016 |
| CN | 205182250 U | 4/2016 |
| CN | 205642979 U | 10/2016 |
| WO | 2013062084 A1 | 5/2013 |

* cited by examiner

EXTRACTION STRUCTURE, EXTRACTION MODULE, AND LIQUID PRETREATMENT DEVICE

RELATED APPLICATIONS

This application claims priority to Chinese Application No. 201610324081.X, filed May 16, 2016, the teachings of which are incorporated herein by reference.

TECHNICAL FIELD

The present invention relates to the technical field of liquid component testing, and particularly to an extraction structure, an extraction module, and a liquid pretreatment device.

BACKGROUND ART

As for traditional treatment modes prior to testing of a liquid sample to be tested, it generally involves steps of sampling, sample preparation, weighing, liquid-liquid partition extraction, solid phase extraction purification, sample filtration, sample transferring and the like. These steps currently are operated stepwise and independently: for example, after completion of the steps of sampling, sample preparation, and weighing of the liquid sample to be tested, a separate appliance and a step are required for performing liquid-liquid partition extraction, then another appliance or apparatus is used for performing the step of solid phase extraction purification, and then a further apparatus or appliance is required to be used for performing the step of sample filtration, and finally the same applies to sample transferring.

At present, the liquid-liquid partition extraction requires a special glass bottle for liquid-liquid partition, so as to oscillate water and a solvent immiscible with water, and make the same stand and layered, and then release a lower layer via a valve, hereby completing the partition process; and it is also reported that diatomite is used to perform the liquid-liquid partition. Both methods mentioned above have the disadvantage that both require to use an individual appliance, cannot be compatible with and performed simultaneously with other steps, need to consume a massive amount of organic solvent, and generally also need a subsequent step of concentration under a reduced pressure for completion.

As for the step of solid phase extraction, a purification step is most commonly used at present. The current solid phase extraction step comprises filling a tube in the form of an injector with a solid phase extractant, and using a vacuum pump from below for forming a vacuum state such that the liquid carries the sample to pass through the solid phase extractant, hereby completing the solid phase extraction process. The completion of this step requires the configuration of a special vacuum pump and a chamber device, and cannot be compatible with other steps to be performed together. Alternatively, without using the tube in the form of an injector, a solid phase extractant is directly added to the liquid sample to be tested, for the purpose of absorbing impurities, but it has the disadvantage that extraction effect is undesirable, and that after completion of the extraction step, a filtrating or centrifuging step is inevitably required for separating the solid phase extractant from the purified sample.

Current step of sample filtration comprises transferring the liquid of the sample to be tested using a special appliance into an injector or a tube having a function of the same type, and pushing and compressing the sample within the injector using a piston, such that the sample passes through a filter membrane mounted at the bottom of the injector, hereby achieving the purpose of filtration. Finally, the filtrated sample is transferred into a corresponding glass bottle.

All the current pretreatment steps (liquid-liquid extraction, solid phase extraction purification, sample filtration, and sample transferring) of a liquid sample to be tested are performed separately, wherein the steps are tedious, and the solvent might be easily contaminated during the processes of filtration, purification and transferring, leading to the problem of inaccurate test results; moreover, multiple steps require multiple specialized appliances to be used and a greater amount of organic solvent to be consumed, influencing the stability and accuracy of the test results, and resulting in greater emission of harmful substances.

DISCLOSURE OF THE INVENTION

An object of the present invention is to provide an extraction structure, an extraction module, and a liquid pretreatment device, so as to solve the technical problems existing in the prior art, such as tedious operation steps, inaccurate test results, production of excessive wastes, and a complicated structure.

The present invention provides an extraction structure, which comprises an extraction structure body, wherein the extraction structure body is provided therein with a cavity and a first pore passage, and a first filter disc, an extractant layer, and a porous filter disc are successively provided within the cavity.

The first filter disc contains therein an expansive agent, forming a filter disc that clogs when encountering water, wherein said filter disc allows passing of an organic solvent, and upon in contact with an aqueous solution, the expansive agent in said filter disc expands rapidly, thereby blocking gaps in the filter disc, so that the aqueous solution cannot pass.

By arranging the first filter disc, the extractant layer and the porous filter disc, said extraction structure can achieve the effects of water blocking, purification and filtration, and can implement the processes of liquid-liquid partition and solid phase extraction in one step.

Further, below the first filter disc is provided a second filter disc, which firstly filters the organic solvent that enters the extraction structure, avoiding the first filter disc from being blocked by large granular impurities in the organic solvent containing at least one component to be tested.

Further, both a bottom and a top of the extraction structure body are configured to be of a taper structure, wherein the taper structure of the bottom of the extraction structure body enables an organic solvent layer to be converged.

Further, a top of the cavity is also configured to be of a taper structure, avoiding the organic solvent from being blocked within the cavity.

Further, a sealing structure is also provided outside the extraction structure body, wherein the sealing structure is provided such that the extraction structure, when being inserted into a container, can be sealed through the sealing structure.

The present invention further provides an extraction module, which comprises an extraction module body, wherein the extraction module body, successively bottom up, comprises a first cavity, a first pore passage, and a second cavity.

The first pore passage is provided therein with a first filter layer, the first cavity is provided therein with a second filter layer, and both the first filter layer and the second filter layer contain therein an expansive agent, forming filter discs that clogs when encountering water.

The second cavity is, successively bottom up, provided therein with an extractant layer and a porous filter disc.

A diameter of the first filter layer is smaller than that of the second filter disc.

Further, a bottom end of the second filter layer is designed to be of a triangular pyramid structure, enabling an organic solvent layer to be converged.

Further, a guide structure is provided outside the extraction module body and provides a guiding function during the movement of the extraction module.

Further, a bottom of the extraction module body is configured to be of a triangular pyramid structure, enabling the organic solvent layer to be converged.

Further, a sealing structure is further provided outside the extraction module body, such that the extraction module, when being inserted into a container, can be sealed through the sealing structure.

Further, a top of the extraction module body is provided with a collecting tube, and the collecting tube is integrated with the extraction module body as one piece.

The present invention further provides a liquid pretreatment device, which comprises a storage tank, a transfer device, and the extraction module, wherein the transfer device is clapped and connected with the extraction module, the extraction module is inserted into the interior of the storage tank, and the storage tank has been already filled with an organic solvent and water which are immiscible with each other and thus layered; and the organic solvent at the upper layer within the storage tank is enabled to pass through the extraction module by pressing the transfer device, and through further pressing, upon in contact with the water layer, the first filter layer and the second filter layer that clog when encountering water are blocked off, and thus the aqueous solution cannot pass, which facilitates the transferring of the liquid of the organic solvent containing at least one component to be tested.

Further, between the transfer device and the extraction module is provided a microporous filter membrane for filtering and supporting, to further filter the separated organic solvent, which makes the test results of the collected organic solvent more accurate.

Further, a bottom of the transfer device is configured to be of a triangular pyramid structure, avoiding the filtered organic solvent from being blocked at the bottom of the transfer device, and to cooperate with the top of the extraction module in use, further avoiding the microporous filter membrane from being blocked.

Further, a second pore passage is provided within the transfer device.

Further, the storage tank is provided thereon with a storage cover, which is in threaded connection with the storage tank.

The beneficial effects of the present invention are as follows:

The extraction structure provided in the present invention can achieve the effects of water blocking, purification and filtration through the arrangement of the first filter disc, the extractant layer, and the porous filter disc, and can implement the processes of liquid-liquid partition and solid phase extraction in one step, wherein the operation steps are simple and the above-mentioned steps can be completed with just one appliance.

The extraction module provided in the present invention can achieve the effects of water blocking, purification and filtration through the arrangement of the first filter layer, the second filter layer, the extractant layer and the porous filter disc, wherein the organic solvent firstly passes through the second filter layer to filter out large granular impurities, and then passes through the first filter layer, avoiding the first filter layer from being blocked by the impurities; as an expansive agent is contained in the second filter layer, gaps within the second filter layer can be blocked, so that the aqueous solution cannot pass, which facilitates the transferring of the organic solvent, hereby completing the liquid extraction process; if the aqueous solution enters the first filter layer before the expansive agent in the second filter layer is able to function in time, due to that the first filter layer has a relatively small diameter and an even less pores, the aqueous solution can be blocked more easily by the expansive agent in the first filter layer, so that the aqueous solution can be thoroughly blocked and completely cannot enter the extractant layer; and then through the extractant layer and the porous filter disc, the processes of liquid-liquid partition and solid phase extraction can be implemented in one step, wherein operation steps are simple and the above-mentioned steps can be completed with just one appliance.

The liquid pretreatment device provided in the present invention can perform filtering and transferring of a sample just in one step, and can make the component test results of the obtained organic solvent more accurate by performing many times of filtration on the organic solvent.

By the cooperative use of the extraction module and the sample transfer device provided in the present invention, the processes of liquid-liquid partition, solid phase extraction, sample filtration, and sample transferring can be completed just in one step.

BRIEF DESCRIPTION OF THE DRAWINGS

In order to more clearly describe specific embodiments of the present invention or technical solutions in the prior art, the drawings to be used in the description of the specific embodiments or the prior art will be simply presented below; and obviously, the drawings in the following description are certain embodiments of the present invention, and for a person skilled in the art, further drawings could be obtained according to these drawings without inventive efforts.

REFERENCE SIGNS 1-transfer device;
2-filter membrane;
3-extraction structure body;
3'-extraction module body;
4-storage tank;
5-guide structure;

11-second pore passage;
31-first pore passage;
32-sealing structure;
33-cavity;
330-first cavity;
34-tray;
35-second cavity;
41-storage cover;
311-first filter layer;
321-second filter layer;
331-porous filter disc;
332-extractant layer;
333-first filter disc;
334-second filter disc;
361-collecting tube.

DETAILED DESCRIPTION OF THE EMBODIMENTS

In the following contents, clear and complete description regarding the technical solutions of the present invention will be made with reference to the drawings, and obviously, the described examples are merely some but not all examples of the present invention. Based on the examples in the present invention, all further examples that could be obtained by a person skilled in the art without inventive efforts fall in the scope of protection of the present invention.

In the description of the present invention, it shall be clarified that orientation or position relationships indicated by terms, such as "central", "upper", "lower", "left", "right", "vertical", "horizontal", "inner", and "outer", are orientation or position relationships shown based on the drawings, only for facilitating the description of the present invention and for simplifying the description, rather than indicating or implying that the specified device or element must have a specific orientation, and be constructed and operated in a certain orientation, and therefore cannot be construed as limiting the present invention. In addition, terms such as "first", "second", and "third" are used merely for purpose of description, and cannot be construed as indicating or implying to have importance in relativity.

In the depiction of the present invention, it shall be clarified that, unless otherwise expressly specified and defined, terms such as "mount", "connect", and "connection" shall be construed in a broad sense. For example, it could be either a fixed connection, or a detachable connection, or an integrated connection; it could be either a mechanical connection, or an electrical connection; and it could be either a direct connection, or an indirect connection through an intermediate, or an inner communication between two elements. For a person skilled in the art, the specific meanings of the above-mentioned terms in the present invention could be construed in accordance with specific circumstances.

In the following contents, the present invention will be further described in detail by means of specific examples with reference to the drawings.

An extraction structure provided in the present invention comprises an extraction structure body, wherein the extraction structure body is provided therein with a cavity and a first pore passage, and a first filter disc, an extractant layer, and a porous filter disc are successively provided within the cavity.

The first filter disc contains therein an expansive agent, forming a filter disc that clogs when encountering water, wherein said filter disc allows passing of an organic solvent, and upon in contact with an aqueous solution, the expansive agent in said filter disc expands rapidly, thereby blocking gaps in the filter disc so that the aqueous solution cannot pass.

By arranging the first filter disc, the extractant layer, and the porous filter disc, said extraction structure can achieve the effects of water blocking, purification and filtration, and can implement the processes of liquid-liquid partition and solid phase extraction in one step.

An extraction module provided in the present invention comprises an extraction module body, wherein the extraction module body, successively bottom up, comprises a first cavity, a first pore passage, and a second cavity; the first pore passage is provided therein with a first filter layer, the first cavity is provided therein with a second filter layer, both the first filter layer and the second filter layer contains therein an expansive agent, forming filter discs that clog when encountering water, said filter disc allows passing of an organic solvent, and upon in contact with an aqueous solution, the expansive agent in said filter disc expands rapidly, thereby blocking gaps in the filter disc, so that the aqueous solution cannot pass; the second cavity is, successively bottom up, provided therein with an extractant layer and a porous filter disc, achieving the effects of water blocking, purification and filtration and realizing implementation of the processes of liquid-liquid partition and solid phase extraction in one step; and a diameter of the first filter layer is smaller than the diameter of the second filter layer.

This extraction module can achieve the effects of water blocking, purification and filtration through the arrangement of the first filter layer, the second filter layer, the extractant layer, and the porous filter disc, and can implement the processes of liquid-liquid partition and solid phase extraction in one step.

Example 1

Figure 1:
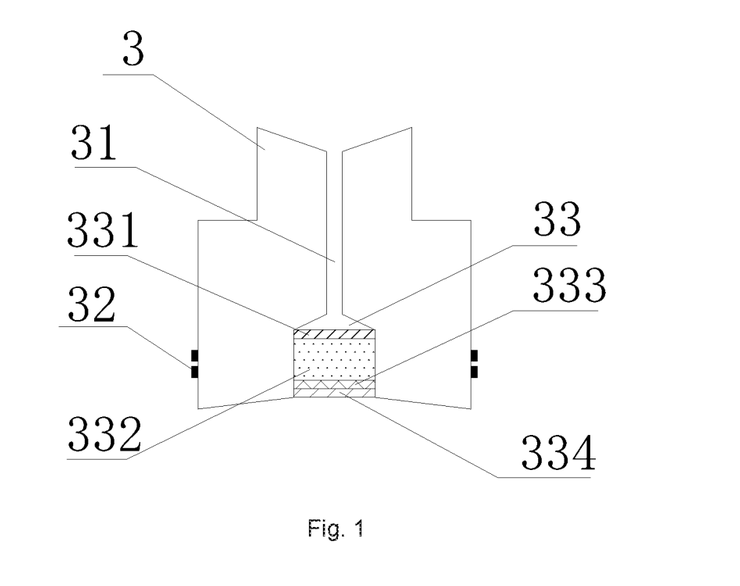
FIG. 1 is a structural schematic view of an extraction structure provided in an example of the present invention.

FIG. 1 is a structural schematic view of an extraction structure provided in an example of the present invention; and as shown in FIG. 1, the extraction structure provided in the present example comprises an extraction structure body 3, wherein the extraction structure body 3 is provided therein with a cavity 33 and a first pore passage 31, and a first filter disc 333, an extractant layer 332, and a porous filter disc 331 are successively provided within the cavity 33.

The first filter disc 333 contains therein an expansive agent, forming a filter disc that clogs when encountering water, wherein said filter disc allows passing of an organic solvent, and upon in contact with an aqueous solution, the expansive agent in said filter disc expands rapidly, thereby blocking gaps in the filter disc so that the aqueous solution cannot pass.

By arranging the first filter disc 333, the extractant layer 332 and the porous filter disc 331, said extraction structure can achieve the effects of water blocking, purification and filtration, and can implement the processes of liquid-liquid partition and solid phase extraction in one step.

In an optional solution of the present example, a pore diameter within the first filter disc 333 is configured to be between 8 μm and 80 μm, which enables rapid passing of the organic solvent, and gaps in the first filter disc 333 can be blocked rapidly through the expansive agent which is expanded upon in contact with the aqueous solution.

In an optional solution of the present example, below the first filter disc 333 is provided a second filter disc 334, which firstly filters the organic solvent that enters the extraction structure, avoiding the first filter disc from being blocked by large granular impurities in the organic solvent containing at least one component to be tested;

wherein the second filter disc 334 is a filter disc with large pore diameters, which is able to avoid the first filter disc 333 from being blocked by the large granular impurities in the organic solvent;

the pore diameter of the second filter disc 334 is configured to be between 40 μm and 120 μm.

In an optional solution in the present example, the porous filter disc 331 is configured to be a polyethylene filter disc for obstructing an extractant from entering into the interior of the first pore passage 31.

In an optional solution of the present example, both a top and a bottom of the extraction structure body 3 are configured to be of a taper structure;

wherein the taper structure of the bottom of the extraction structure body 3 enables an organic solvent layer to be converged.

In an optional solution of the present example, a top of the cavity 33 is also configured to be of a taper structure, avoiding the filtered organic solvent from being blocked within the cavity 33.

In an optional solution of the present example, the taper structure is configured to be a cone structure or a triangular pyramid structure.

In an optional solution of the present example, a sealing structure 32 is also provided outside the extraction structure body 3, wherein the sealing structure 32 is provided such that the extraction structure, when being inserted into a container, can be sealed through the sealing structure 32.

The sealing structure 32 can be configured as a sealing ring or a sealing pad.

In an optional solution of the present example, a tray 34 is further provided outside the extraction structure body 3, which is used for placing a container configured for collecting the transferred organic solvent.

Referring to the detailed description of the present invention above, it can be seen that the extraction structure provided in the present example can achieve the effects of water blocking, purification and filtration through the arrangement of the first filter disc 333, the extractant layer 332 and the porous filter disc 331, and can implement the processes of liquid-liquid partition and solid phase extraction in one step, which makes the extraction step more simple; moreover, by arranging a bilayer filtering structure, the extraction process is enabled to be more smooth, and the extracted organic solvent has less impurities.

Example 2

Figure 2:
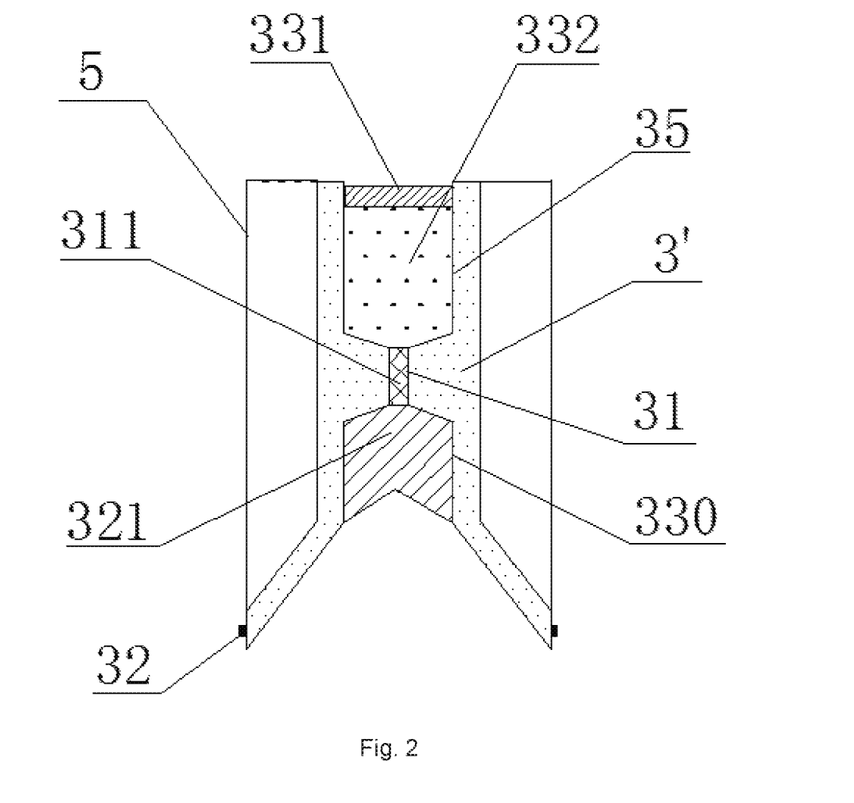
FIG. 2 is a structural schematic view of an extraction module provided in an example of the present invention.

FIG. 2 is a structural schematic view of an extraction module provided in an example of the present invention; as shown in FIG. 2, the extraction module provided in the present example comprises an extraction module body 3', wherein the extraction module body 3', successively bottom up, comprises a first cavity 330, a first pore passage 31, and a second cavity 35; the first pore passage 31 is provided therein with a first filter layer 311, the first cavity 330 is provided therein with a second filter layer 321, both the first filter layer 311 and the second filter layer 321 contain therein an expansive agent, forming filter discs that clog when encountering water, the filter discs allow passing of an organic solvent, and upon in contact with an aqueous solution, the expansive agent in filter discs expands rapidly, thereby blocking gaps in the filter disc, so that the aqueous solution cannot pass; the second cavity 35 is, successively bottom up, provided therein with an extractant layer 332 and a porous filter disc 331, achieving the effects of water blocking, purification and filtration and realizing implementation of the processes of liquid-liquid partition and solid phase extraction in one step; and the diameter of the first filter layer 311 is smaller than that of the second filter layer 321.

This extraction module can achieve the effects of water blocking, purification and filtration through the arrangement of the first filter layer 311, the second filter layer 321, the extractant layer 332, and the porous filter disc 331, and can implement the processes of liquid-liquid partition and solid phase extraction in one step, which makes the extraction step more simple; moreover, by arranging a bilayer filtering structure, the extraction process is enabled to be more smooth, and the extracted organic solvent has less impurities.

During use of the extraction module, the organic solvent firstly passes through the second filter layer 321 to filter out large granular impurities, and then passes through the first filter layer 311, avoiding the first filter layer 311 from being blocked by the impurities; as the expansive agent is contained in the second filter layer 321, gaps within the second filter layer 321 can be blocked, so that the aqueous solution cannot pass, which facilitates transferring of the organic solvent, hereby completing the liquid extraction process; and sometimes there might be accidental circumstances, i.e. the aqueous solution enters the first filter layer 311 before the aqueous solution passes through the second filter layer 321 and the expansive agent in the second filter layer 321 is not able to function in time, or when the aqueous solution infiltrates laterally through the second filter layer 321, and in this case, due to that the first filter layer 311 has a relatively small diameter and an even less pores, the aqueous solution can be blocked more easily by the expansive agent in the first filter layer 311, so that the aqueous solution can be thoroughly blocked and completely cannot enter the extractant layer 332.

It shall be indicated that in the case that the first filter layer 311, the second filter layer 321, the extractant layer 332, and the porous filter disc 331 are disposed within a same chamber, some small particles might be adsorbed on an inner wall of the chamber of the extraction module due to static electricity, when disposing the extractant layer 332, and thus, during mounting of the first filter layer 311 and the second filter layer 321, the small particles might be clamped between inner walls of the chamber and side faces of the first filter layer 311 and the second filter layer 321, which easily leads to the problem that the aqueous solution infiltrates laterally and is mixed with the organic solvent, resulting in a failed extraction. The present invention solves the problem by making the aqueous solution be thoroughly blocked and not be able to enter the extractant layer 332.

It shall be further indicated that during mounting, the first filter layer 311 is firstly mounted, then the second filter layer 321 is mounted, and then the extraction module is inversed so that the extractant layer 332 and the porous filter disc 331 are successively filled from the entrance of the second cavity 35, and then the extractant layer 332 is fixed.

It shall be further indicated that a bottom end of the second filter layer 321 is designed to be of a triangular pyramid structure, and forms, together with the triangular pyramid structure of the extraction module, an inverted funnel shape, facilitating the converging of the organic solvent at the upper layer and ensuring that all the organic solvent can pass through the second filter layer 321 without leaving any residue; moreover, the contact area of the second filter layer 321 and the organic solvent can further be increased, which enables a greater capacity of filtering the organic solvent at the upper layer and a greater capacity of adsorbing the granular impurities within the organic solvent layer, and thus hardly would result in blocking.

In an optional solution of the present example, a guide structure is provided outside the extraction module body 3', and provides a guiding function during the movement of the extraction module, so that the extraction module would not be deflected during downward movement; moreover, the design of the guide structure enables the extraction module to be designed to be thinner and consumes less materials, which not only saves materials but also is beneficial to environmental protection.

In an optional solution of the present example, a bottom of the extraction module body 3' is configured to be of a triangular pyramid structure, enabling the organic solvent layer to be converged.

In an optional solution of the present example, a sealing structure 32 is further provided outside the extraction module body 3', wherein the sealing structure 32 is provided so that the extraction module, when being inserted into a container, can be sealed through the sealing structure 32.

The sealing structure 32 can be configured as a sealing ring or a sealing pad.

In an optional solution of the present example, the porous filter disc 331 is configured to be a polyethylene filter disc for fixing the extractant.

In an optional solution of the present example, a top of the first cavity 330 is also configured to be of a triangular pyramid structure, avoiding the filtered organic solvent from being blocked within the first cavity 330.

Example 3

Figure 3:
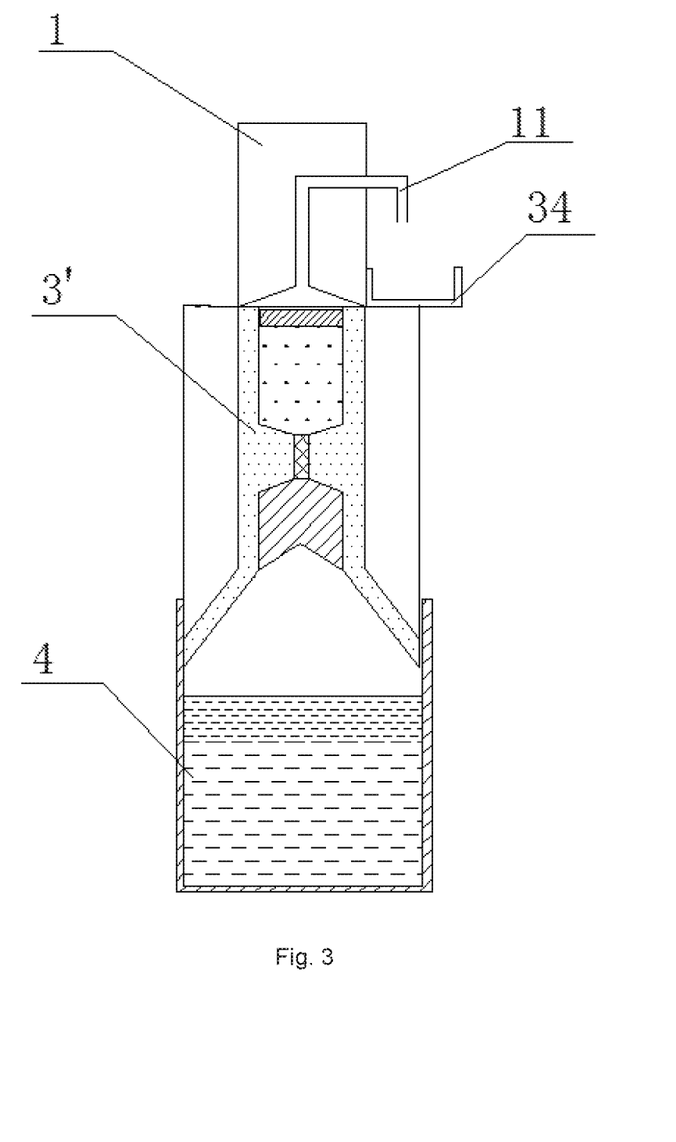
FIG. 3 is a structural schematic view of a liquid pretreatment device comprising an extraction module provided in an example of the present invention.
Figure 4:
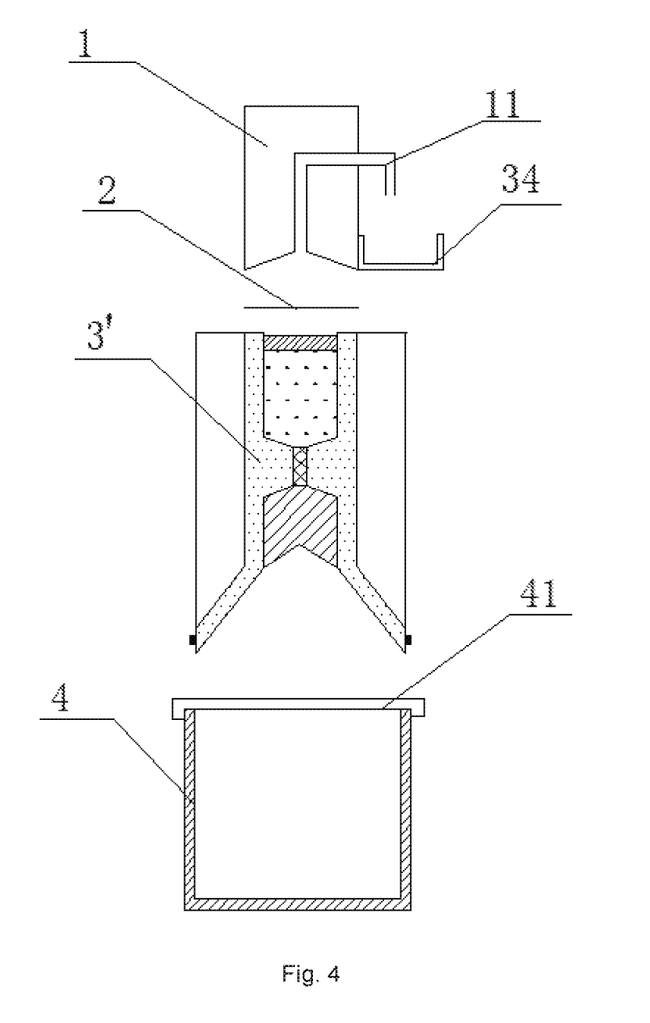
FIG. 4 is an exploded view of the liquid pretreatment device as shown in FIG. 3.

FIG. 3 is a structural schematic view of a liquid pretreatment device comprising an extraction module provided in the present invention; FIG. 4 is an exploded view of the liquid pretreatment device as shown in FIG. 3; and as shown in FIGS. 3 and 4, the liquid pretreatment device provided in the present example comprises a storage tank 4, a transfer device 1, and the extraction module, wherein the transfer device 1 is clapped and connected with the extraction module, the extraction module is inserted into the interior of the storage tank 4, and the storage tank 4 has been already filled with an organic solvent and water, which are immiscible with each other and thus layered; and the organic solvent at the upper layer within the storage tank 4 is enabled to pass through the extraction module by pressing the transfer device 1, and through further pressing, when the first filter layer 311 and the second filter layer 321 that clog when encountering water are in contact with the water layer, the first filter layer 311 and the second filter layer 321 are blocked off, and thus the aqueous solution cannot pass, which facilitates transferring of the liquid of the organic solvent containing at least one component to be tested, hereby implementing the four operations of liquid-liquid extraction, solid phase extraction purification, sample filtration and sample transferring just in one step.

In an optional solution of the present example, between the transfer device 1 and the extraction module is provided a microporous filter membrane 2 for filtering and supporting, which serves for further filtering the organic solvent separated from the aqueous solution:

wherein a pore diameter within the microporous filter membrane 2 is configured to be between 0.2 μm and 0.5 μm.

Thus, the test results of the collected organic solvent can be made more accurate through many times of filtration of the organic solvent.

In an optional solution of the present example, a bottom of the transfer device 1 is configured to be of a triangular pyramid structure, avoiding the filtered organic solvent from being blocked at the bottom of the transfer device 1, and is in cooperative use with the triangular pyramid structure of the top of the extraction module body 3', further avoiding the microporous filter membrane 2 from being blocked.

In an optional solution of the present example, a second pore passage 11 is provided within the transfer device 1, which facilitates outflowing of the organic solvent.

In an optional solution of the present example, the storage tank 4 is provided thereon with a storage cover 41, wherein the storage cover 41 is in threaded connection with the storage tank 4, and when transferring the solution, the organic solvent can be discharged out just by inserting the extraction module and the transfer device 1, which are assembled, into the inside of the storage tank 4 and performing pressing.

In an optional solution of the present example, a tray 34 is also provided at one side of the transfer device 1, and the tray 34 is provided in correspondence with a pore passage at the other side of the second pore passage 11.

Example 4

Figure 5:
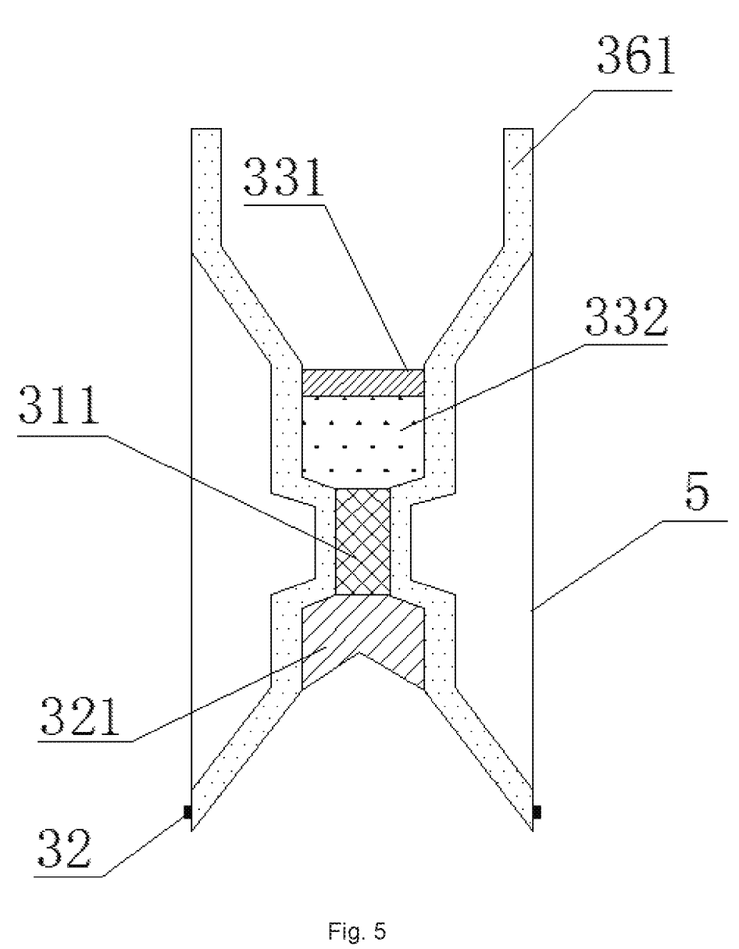
FIG. 5 is a structural schematic view of an extraction module provided in another example of the present invention.

FIG. 5 is a structural schematic view of an extraction module provided in another example of the present invention; and as shown in FIG. 5, the extraction module provided in the present example comprises an extraction module body 3', wherein the extraction module body 3', successively bottom up, comprises a first cavity 330, a first pore passage 31, and a second cavity 35; the first pore passage 31 is provided therein with a first filter layer 311, and the first cavity 330 is provided therein with a second filter layer 321, both the first filter layer 311 and the second filter layer 321 contain therein an expansive agent, forming filter discs that clog when encountering water, said filter disc allows passing of an organic solvent, and upon in contact with an aqueous solution, the expansive agent in said filter disc expands rapidly, thereby blocking gaps in the filter disc, so that the aqueous solution cannot pass; the second cavity 35 is, successively bottom up, provided therein with an extractant layer 332 and a porous filter disc 331, achieving the effects of water blocking, purification and filtration and realizing implementation of the processes of liquid-liquid partition and solid phase extraction in one step; and a diameter of the first filter layer 311 is smaller than that of the second filter layer 321.

In an optional solution of the present example, a top of the extraction module body 3' is provided with a collecting tube 361, and the collecting tube 361 is integrated with the extraction module body 3' as one piece.

When the extraction module is inserted into the interior of the storage tank, the storage tank has been already filled with an organic solvent and water which are immiscible with each other and thus layered; and the organic solvent at the upper layer within the storage tank is enabled to contact the second filter layer 321 and the first filter layer 311 by pressing the collecting tube 361 of organic solvent, and the second filter layer 321 and the first filter layer 311 are porous filter discs 331 containing an expansive agent therein, wherein the organic solvent can smoothly pass through the second filter layer 321 and the first filter layer 311, and enter the extractant layer 332 and the porous filter disc 331, the impurities in the organic solvent are adsorbed by the extractant, and finally the organic solvent layer enters the collecting tube 361 of organic solvent; through further pressing, when the second filter layer 321 and the first filter layer 311 that clog when encountering water are in contact with the water layer, the second filter layer 321 and the first filter layer 311 both are blocked off, and thus the aqueous solution cannot pass; and the four operations of liquid-liquid partition, solid phase extraction purification, sample filtration, and sample transferring can be implemented in one step.

At last, it shall be clarified that the above-mentioned respective examples are only used for describing the technical solutions of the present invention, rather than limiting the same; although the present invention is described in detail with reference to the preceding respective examples, it shall be understood for a person skilled in the art that the technical solutions recorded in the preceding respective examples could still be modified, or partial or all technical features thereof could be substituted in an equivalent way; and the modifications or substitutions do not make the essence of the corresponding technical solutions depart from the scope of the technical solutions of the respective examples of the present invention.

The invention claimed is:

1. An extraction structure, comprising:
   an extraction structure body, wherein the extraction structure body is provided therein with a cavity and a first pore passage, and a first filter disc, an extractant layer and a porous filter disc are successively provided within the cavity; and
   the first filter disc contains therein an expansive agent, the expansive agent configured to expand when encountering water and when expanded block passage through the first filter disc,
   wherein both a top and a bottom of the extraction structure body are configured to be of a taper structure, and wherein a top of the cavity is also configured to be of a taper structure.

2. The extraction structure according to claim 1, wherein below the first filter disc is provided a second filter disc which is configured for filtering out large granular impurities.

3. The extraction structure according to claim 1, wherein a sealing structure is provided outside the extraction structure body.

4. An extraction module comprising:
   an extraction module body, wherein the extraction module body comprises a first cavity, a first pore passage, and a second cavity sequentially from bottom to top, the first pore passage is provided therein with a first filter layer, the first cavity is provided therein with a second filter layer, and both the first filter layer and the second filter layer contain therein an expansive agent;
   the second cavity is provided therein with an extractant layer and a porous filter disc sequentially from bottom to top; and
   a diameter of the first filter layer is smaller than that of a second filter disc,
   wherein a bottom end of the second filter layer is configured to be of a triangular pyramid structure, and wherein a bottom of the extraction module body is configured to be of a triangular pyramid structure.

5. The extraction module according to claim 4, wherein a guide structure is provided outside the extraction module body.

6. The extraction module according to claim 4, wherein a sealing structure is further provided outside the extraction module body.

7. The extraction module according to claim 5, wherein a sealing structure is further provided outside the extraction module body.

8. The extraction module according to claim 4, wherein a top of the extraction module body is provided with a collecting tube, and the collecting tube is integrated with the extraction module body as one piece.

9. A liquid pretreatment device, comprising a storage tank, a transfer device, and the extraction module according to claim 4, wherein the transfer device is clapped and connected with the extraction module, and the extraction module is inserted into an interior of the storage tank.

10. The liquid pretreatment device according to claim 9, wherein between the transfer device and the extraction module is provided a filter membrane configured for filtering and supporting.

11. The liquid pretreatment device according to claim 9, wherein a bottom of the transfer device is configured to be of a triangular pyramid structure.

12. The liquid pretreatment device according to claim 10, wherein a bottom of the transfer device is configured to be of a triangular pyramid structure.

13. The liquid pretreatment device according to claim 9, wherein a second pore passage is provided within the transfer device.

* * * * *